United States Patent [19]

Panoch et al.

[11] Patent Number: 4,981,571

[45] Date of Patent: Jan. 1, 1991

[54] MEMBRANE FOR BARIUM ION SELECTIVE ELECTRODE

[75] Inventors: Miroslav Panoch, Turnov; Miloslav Semler, Přepeře; Břetislav Mánek, Železný Brod; Miloslav Kolínsky, Prague, all of Czechoslovakia

[73] Assignee: Ceskoslovenska akademie ved, Prague, Czechoslovakia

[21] Appl. No.: 336,043

[22] Filed: Apr. 11, 1989

[30] Foreign Application Priority Data

Apr. 12, 1988 [CS] Czechoslovakia .............. PV2493-88

[51] Int. Cl.$^5$ .......................................... G01N 27/333
[52] U.S. Cl. ........................................ 204/418; 560/45
[58] Field of Search .................. 204/418, 1 A; 560/45

[56] References Cited

FOREIGN PATENT DOCUMENTS 217537 2/1985 Czechoslovakia .

OTHER PUBLICATIONS

M. Güggi et al., Analytica Chimica Acta, 91, 107. 112, (1977).
Karl Cammann, "Working With Ion-Selective Electrodes", pp. 28 84 & 85, (1979).

*Primary Examiner*—G. L. Kaplan
*Attorney, Agent, or Firm*—Leydig, Voit & Mayer

[57] ABSTRACT

Membrane for barium ion selective electrode

The solution pertains to a membrane for barium ion selective electrode formed by the film of suitable polymeric material, for example, high-molecular weight poly(vinyl chloride), with an ion exchanger based on a neutral carrier, namely N,N'-diphenyl-N,N'-di-(2-n-butyloxycarbonylphenyl)diamide of 3,6,9-trioxaundecandioic acid

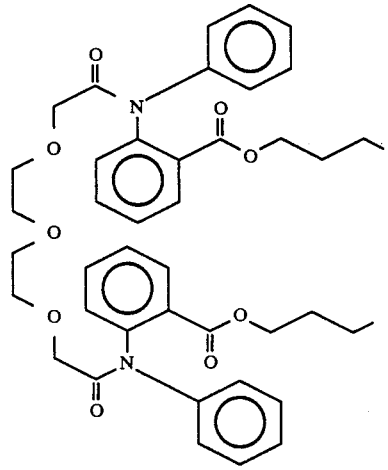

4 Claims, No Drawings

MEMBRANE FOR BARIUM ION SELECTIVE ELECTRODE

BACKGROUND OF THE INVENTION

The invention pertains to a membrane for the barium ion selective electrode, more exactly to a ligand which is a part of complex barium salt forming an active component of a membrane.

Among the new types of ion selective electrodes, which occur in literature and have been on the market in last years, is the barium ion selective electrode. Simon and coworkers were concerned with the preparation and application of this type of electrode based on so called "neutral carriers"-derivatives of oligoglycolic acids (Analytica Chimica Acta 91, 107–112, 1977). Electrodes based on derivatives of 3,6,9-trioxaundecandioic acid are further described in the Czechoslovak patent No. 217,537.

The hitherto known electrodes have a short service life and low selectivity.

SUMMARY OF THE INVENTION

The barium ion selective electrodes according to the invention exhibit selective properties improved in many respects. These electrodes have a membrane formed by a solution of a new complex barium (II) salt in nitrated aryl alkyl ethers fixed in a matrix of a suitable polymer, for example, high-molecular weight poly(vinyl chloride), where the said complex barium (II) salt has the schematic formula $(L_2.Ba)(X)_2$, 

where Ba is barium (II) cation and X is the suitable lipophilic anion, for example, tetraaryl borate anion and L is a ligand, said ligand L being according to the invention the N,N'-diphenyl-N,N'-di-(2-n-butyloxycarbonylphenyl)diamide of 3,6,9-trioxaundecandioic acid of structure formula

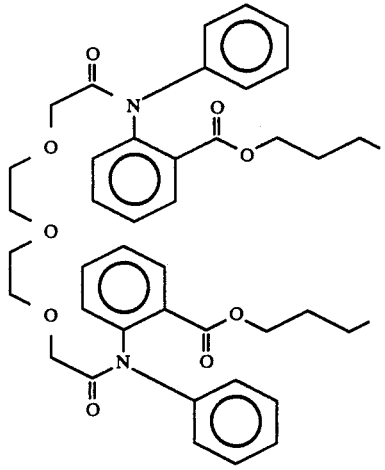

As the lipophilic anion there is advantageously used the tetraaryl borate anion especially the tetraphenyl borate anion, tetra-p-diphenyl borate anion, tetra-p-chlorphenyl borate anion etc.

DETAILED DESCRIPTION OF THE PREFERRED EMBODIMENTS

The barium ion selective electrode containing the membrane according to the invention has better selective properties and a longer service life than the hitherto known electrodes.

The electrodes according to the invention are used in particular in evaluation of mineral engine oils (the determination of the content of active barium) and in agriculture for the determination of sulfates, etc.

Compositions and properties of the prepared and used membranes are given in the examples of performance.

EXAMPLE 1

The plastic film consisting of 38.5 wt.-% high-molecular weight poly(vinyl chloride) (PVC), 59,8 wt.-% o-nitrophenyl n-octyl ether (o-NPOE), and 1.7 wt.-% complex barium (II) salt ($L_2.Ba$) (TPB)$_2$, where Ba is barium (II) cation, TPB is the lipophilic tetraphenyl borate anion, and L is the ligand, "neutral carrier", according to the invention, viz. N,N'-diphenyl-N,N'-di-(2-n-butyloxycarbonylphenyl)diamide of 3,6,9-trioxaundecandioic acid, was prepared in the common way, i.e. by casting from a solution in cyclohexanone. The film was used as a membrane of a barium ion selective electrode with the reference electrolyte $BaCl_2$, c=0.1 mol/l, and internal reference electrode Ag/AgCl. The electrode was measured in a cell with saturated calomel electrode. Measurements were carried out in water solutions at 293±2 K. The electrode response to the activity of barium (II) ions was measured in solutions of $BaCl_2$ in the concentration range c=$10^{-6}-10^{-1}$ mol/l; pH of solution was adjusted with tris-hydroxymethylaminomethane, c=0.05 mol/l, and HCl, c=0.04 mol/l, to the value 7.50–7.70. The results of measurements are in Table I, column 1.

Selectivity coefficients $K_{Ba,j}^{Pot}$ 

were measured in the same arrangement by the method of mixed samples using the solutions of chlorides of the pertinent cations, c=0.1 mol/l; pH was adjusted with tris-hydroxymethylaminomethane, c=0.05 mol/l, and HCl, c=0.04 mol/l, to 7.50–7.70. Their values are given in the form log $K_{Ba,j}^{Pot}$ 

in Table II, column 1.

EXAMPLE 2

The plastic film consisting of 38.5 wt.-% PVC, 59.8 wt.-% 2,4-dinitrophenyl n-octyl ether (2,4-DNPOE) and 1.7 wt.-% of the same complex salt as in example 1 was prepared in the same way as in example 1. The film was used similarly as in example 1 as a membrane of barium ion selective electrode with the same reference system. The electrode response to the activity of barium (II) ions and the selectivity coefficients were measured in the same way as in example 1 and are presented in Table I, column 2 and Table II, column 2, respectively.

EXAMPLE 3

The plastic film with composition 38.4 wt.-% PVC, 59.7 wt.-% o-NPOE and 1.9 wt.-% complex barium (II) salt (L$_2$.Ba) (TBPB)$_2$, where L is the same ligand as in example 1, Ba is barium (II) cation and TBPB is the lipophilic tetra-p-biphenylyl borate anion, was made as in example 1. Properties of the film as a membrane of barium ion selective electrode were measured in the same way as in example 1. The electrode response to the activity of barium (II) ions is given in Table I, column 3 and selectivity coefficients in Table II, column 3.

EXAMPLE 4

The plastic film with composition 38.4 wt.-% PVC, 59.7 wt.-% 2,4-DNPOE and 1.9 wt.-% of the same barium (II) salt as in example 3 was made as in example 1. Properties of this film as a membrane of barium ion selective electrode were measured in the same way as in example 1. The electrode response to the activity of barium (II) ions is presented in Table I, column 4 and selectivity coefficients are in Table II, column 4.

TABLE I (Gives the slope of the barium electrode)

Tris-, c = 0.05 mol/l
HCl, c = 0.04 mol/l

| BaCl$_2$, c = (mol/l) | EMS (mV) | | | |
|---|---|---|---|---|
| | 1 | 2 | 3 | 4 |
| 10$^{-6}$ | −105.5 | −95.7 | −95.1 | −97.9 |
| 10$^{-5}$ | −77.3 | −72.2 | −72.2 | −70.6 |
| 10$^{-4}$ | −48.6 | −44.4 | −44.7 | −43.6 |
| 10$^{-3}$ | −20.1 | −16.2 | −16.8 | −16.0 |
| 10$^{-2}$ | +7.6 | +11.2 | +10.4 | +11.2 |
| 10$^{-1}$ | +35.4 | +38.6 | +37.6 | +38.4 |

EMS = electromotive force of the cell.

TABLE II (gives the selectivity coefficients)

| j = | log K$_{Ba,j}^{Pot}$ | | | |
|---|---|---|---|---|
| | 1 | 2 | 3 | 4 |
| NH$_4^+$ | −3.65 | −3.64 | −3.41 | −3.59 |
| Li$^+$ | −3.99 | −3.95 | −3.76 | −3.98 |
| Na$^+$ | −3.61 | −3.31 | −3.33 | −3.52 |
| K$^+$ | −3.09 | −2.82 | −2.97 | −2.83 |
| Rb$^+$ | −3.24 | −3.01 | −3.08 | −3.04 |
| Cs$^+$ | −3.57 | −3.27 | −3.31 | −3.35 |
| Mg$^{2+}$ | below −5 | below −5 | below −5 | below −5 |
| Ca$^{2+}$ | −3.76 | −3.58 | −3.44 | −3.58 |
| Sr$^{2+}$ | −1.40 | −1.20 | −1.29 | −1.34 | j = interfering cation
Pot = potentiometric determination

From table II it can be seen that towards all the cations the electrode is less sensitive than against barium.

We claim:

1. A membrane for use as a barium ion selective electrode comprising a film of a polymeric material containing an ion exchanger based on a complex barium (II) salt having the schematic formula (L$_2$.Ba)(X)$_2$, wherein Ba is a barium (II) cation, X is a lipophilic anion, and L is a ligand which is the N,N'-diphenyl-N,N'-di-(2-n-butyloxycarbonylphenyl)diamide of 3,6,9-trioxaundecandioic acid having the structural formula:

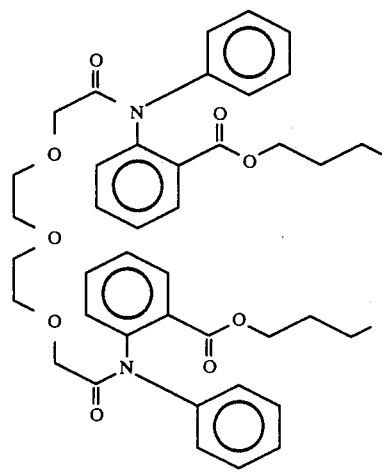

2. The membrane of claim 1 wherein the polymeric material is poly(vinyl chloride).

3. The membrane of claim 2 wherein the lipophiolic anion is tetraarylborate.

4. The membrane of claim 1 wherein the lipophilic anion is tetraarylborate.